United States Patent
Wang

(10) Patent No.: US 11,814,474 B2
(45) Date of Patent: Nov. 14, 2023

(54) CONTROLLED PRODUCTION OF POLYGLYCOLIC ACID AND GLYCOLIDE

(71) Applicant: Pujing Chemical Industry Co., Ltd., Shanghai (CN)

(72) Inventor: Saibo Wang, Shanghai (CN)

(73) Assignee: Pujing Chemical Industry Co., Ltd., Shanghai (CN)

( * ) Notice: Subject to any disclaimer, the term of this patent is extended or adjusted under 35 U.S.C. 154(b) by 391 days.

(21) Appl. No.: 17/289,472

(22) PCT Filed: Oct. 29, 2018

(86) PCT No.: PCT/CN2018/112474
§ 371 (c)(1),
(2) Date: Apr. 28, 2021

(87) PCT Pub. No.: WO2020/087221
PCT Pub. Date: May 7, 2020

(65) Prior Publication Data
US 2021/0395444 A1 Dec. 23, 2021

(51) Int. Cl.
*C08G 63/82* (2006.01)
*C08G 63/06* (2006.01)
*C07F 17/00* (2006.01)

(52) U.S. Cl.
CPC .............. *C08G 63/06* (2013.01); *C07F 17/00* (2013.01); *C08G 63/826* (2013.01)

(58) Field of Classification Search
CPC .......... C08G 63/82; C08G 63/06; C07F 17/00
USPC ........................................................ 524/788
See application file for complete search history.

(56) References Cited

U.S. PATENT DOCUMENTS

2004/0138409 A1  7/2004  Hayashi et al.

FOREIGN PATENT DOCUMENTS

| CN | 101054371 A | * | 10/2007 |
|---|---|---|---|
| CN | 101054371 A | | 10/2007 |
| CN | 101495440 A | | 7/2009 |
| CN | 105061479 A | | 11/2015 |
| CN | 105061734 A | | 11/2015 |
| CN | 105218512 A | | 1/2016 |
| CN | 105272958 A | | 1/2016 |
| CN | 106432697 A | | 2/2017 |
| CN | 107177032 A | | 9/2017 |
| EP | 0789023 A2 | | 8/1997 |
| JP | H11116666 A | | 4/1999 |
| WO | 2004007422 A1 | | 1/2004 |

OTHER PUBLICATIONS

PCT International Search Report and Written Opinion, PCT/CN2018/112474, dated Jul. 25, 2019, 8 pages.

* cited by examiner

*Primary Examiner* — Deve V Hall
(74) *Attorney, Agent, or Firm* — Quarles & Brady LLP

(57) ABSTRACT

Provided is a process for producing a product having polyglycolic acid and glycolide from methyl glycolate. The process comprises esterification, polycondensation and optimization. Also provided are a product produced by the process and a method of changing the amount of the polyglycolic acid in the product by modifying the amount of an esterification catalyst and/or adjusting the reaction temperature.

21 Claims, 1 Drawing Sheet

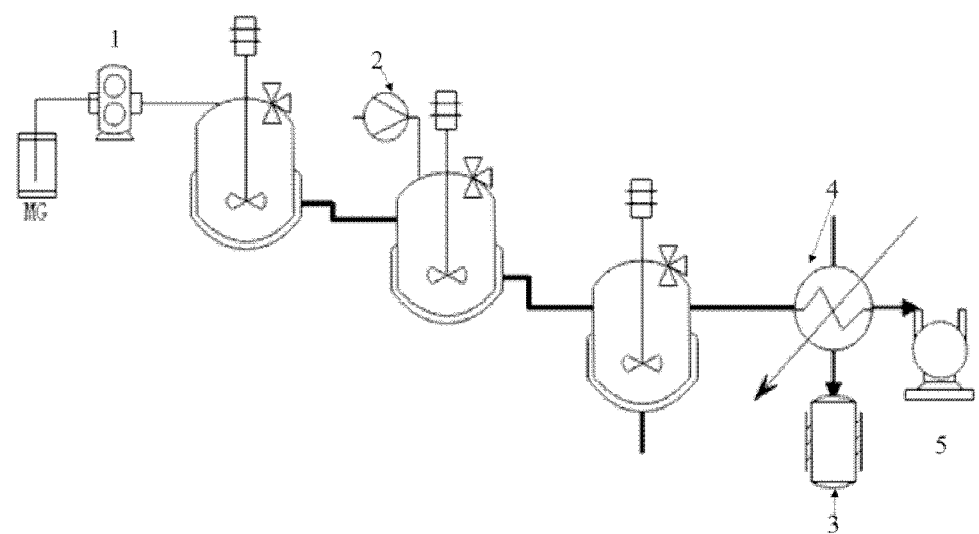

CONTROLLED PRODUCTION OF POLYGLYCOLIC ACID AND GLYCOLIDE

CROSS-REFERENCE TO RELATED APPLICATIONS

This application represents the U.S. national stage entry of International Application No. PCT/CN2018/112474 filed Oct. 29, 2018, the disclosure of which is incorporated herein by reference in its entirety and for all purposes.

FIELD OF THE INVENTION

The invention relates to a process of producing polyglycolic acid and glycolide from methyl glycolate.

BACKGROUND OF THE INVENTION

Polyglycolic acid is the simplest structural aliphatic polyester. It was also the first bioactive absorbable suture material. It has many applications in the medical field, such as drug controlled release systems and solid stents for plastic surgery. Polyglycolic acid has excellent processing properties, high mechanical strength and modulus, high solvent resistance, good biocompatibility, high gas barrier properties and biodegradability. Based on these properties, polyglycolic acid can be used in packaging materials and agricultural biodegradable films in addition to medical materials. There are two ways to synthesize polyglycolic acid. One is achieved by esterification and polycondensation by using a glycolic acid with the action of a tin-based catalyst. As described in Chinese patent application CN106432697A, in order to obtain a high molecular weight polyglycolic acid, this process requires addition of a chain extender to increase viscosity after dehydration refining, catalytic reaction and chain extension reaction. But, when the selected raw material is glycolic acid, methyl glycolate must be hydrolyzed to generate the glycolic acid. The other way is ring-opening polymerization of glycolide. The glycolide must be prepolymerized, pyrolyzed and recrystallized. High molecular weight polyglycolic acid can be easily obtained by this process. However, it is known from Chinese patent application CN107177032A that glycolide is difficult to obtain because its preparation process is complicated, and glycolide has not yet been industrialized. This hinders the industrial production of polyglycolic acid.

A set of equipment and processes previously disclosed can produce only either glycolide or polyglycolic acid. If the target product is changed, the entire process equipment needs to be re-planned, resulting in an increase in production costs. For example, the patent CN105218512B discloses a process for producing glycolide. Two reaction chambers are designed to carry out polymerization of glycolic acid and decomposition of polyglycolic acid in a polymerization reaction chamber and a cyclization reaction chamber, respectively. After the glycolic acid is polymerized, the polyglycolic acid is introduced into the cyclization reaction chamber for rapid decomposition by a stepwise feeding method. The glycolide product is finally collected.

Therefore, there remains an urgent need for a process of producing polyglycolic acid having a high molecular weight, low yellow index and excellent chemical and physical properties as well as a process of controlled production of polyglycolic acid and glycolide.

SUMMARY OF THE INVENTION

The present invention relates to a process for producing polyglycolic acid and glycolide.

A process for producing polyglycolic acid and glycolide from methyl glycolate is provided. The process comprises (a) esterifying methyl glycolate in the presence of an esterification catalyst, whereby a melted pre-esterified polymer is formed; (b) polycondensing the melted pre-esterified polymer in the presence of a polycondensation catalyst, whereby polyglycolic acid based polymer is formed; and (c) optimizing the polyglycolic acid based polymer at an optimization temperature of 200-250, whereby the product containing both polyglycolic acid and glycolide is produced.

The esterification catalyst may comprise a tin salt, a zinc salt, a titanium salt, a sulfonium salt, a tin oxide, a zinc oxide, a titanium oxide, a sulfonium oxide, or a combination thereof. The methyl glycolate and the esterification catalyst may have a molar ratio of $1:(10^{-5}\text{-}10^{-2})$.

The polycondensation catalyst may comprise an oxide, compound or complex of a rare earth element or a combination thereof. The rare earth element may be selected from the group consisting of cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y). The particle of rare earth oxide has the diameter of 2-50 μm, more preferable in the range of 30-45 μm. Suitable materials for the rare earth oxide include, but are not limited to, $La_2O_3$ maybe with the diameter of 35-45 μm, for example 40 μm. The compound of a rare earth is the crystalline carbonate. Suitable materials for the crystalline rare earth carbonate, but are not limited to, crystalline $Ce(HCO_3)_4$. The coordination complex of a rare earth element may be tris (cyclopentadienyl) lanthanum (III) having formula (I):

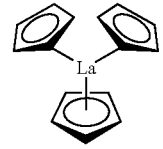

(I)

The methyl glycolate and the rare earth element may have a molar ratio of $1:(10^{-7}\text{-}10^{-4})$.

The polycondensation catalyst may further comprise an inorganic nanofiller selected from the group consisting of nano white carbon black, nano calcium carbonate, carbon nanotube, nanofibers and a combination thereof.

The optimization reaction may comprise devolatilization or final polycondensation reaction of the polyglycolic acid based polymer in a falling strand devolatilizer, a twin screw devolatilizer, a ribbon stirred reactor, a horizontal disc-ring reactor or a twin-axis self-cleaning reactor.

According to the process, the resulting product may contain the glycolide at 1.5-75 wt % and the polyglycolic acid at 25-98.5 wt %, both based on the total weight of the product. The proportion of each product may be adjusted by changing the reaction temperature and content the esterification catalyst.

Where the esterification catalyst is present in an amount less than 0.1 wt % of the total weight of the methyl glycolate, and the optimization temperature is not above 230° C., the product may contain the polyglycolic acid in an amount greater than 95 wt %, based on the total weight of the product. Where the esterification catalyst is present in an amount no less than 0.1 wt % of the total weight of the methyl glycolate, and the optimization temperature is above 230° C., the product may contain the glycolide in an amount greater than 70 wt %, based on the total weight of the products.

The polyglycolic acid produced by the process may have a weight-average molecular weight of 90,000-200,000, an inherent viscosity of 0.8-1.3 dl/g, a yellowness index (YI) of 9-70, and/or a free acid content of glycolide less than 2 wt %, based on the total weight of the polyglycolic acid.

For each process of the invention, a product is produced. The product may contain the glycolide at 1.5-75 wt % and the polyglycolic acid at 25-98.5 wt %, both based on the total weight of the product.

A method of changing the amount of the polyglycolic acid in the product produced by the process of the present invention is provided. The method comprises modifying the amount of the esterification catalyst relative to the total weight of the methyl glycolate, adjusting the optimization temperature, or a combination thereof. The method may further comprise maintaining the esterification catalyst in an amount below 0.1 wt % of the total weight of the methyl glycolate and the optimization temperature not above 230° C. such that the product may contain the polyglycolic acid in an amount greater than 95 wt %, based on the total weight of the product. The method may further comprise maintaining the esterification catalyst in an amount not below 0.1 wt % of the total weight of the methyl glycolate and the optimization temperature above 230° C. such that the product may contain the glycolide in an amount greater than 70 wt %, based on the total weight of the product.

BRIEF DESCRIPTION OF THE DRAWINGS

FIG. 1 is a diagram showing a process for producing polyglycolic acid and glycolide simultaneously from methyl glycolate (MG) according to one embodiment of the invention. In the first stage, methyl glycolate is added via a gear pump (1) into an esterification reactor and reacts with an esterification catalyst to form a melted pre-esterified polymer. In the second stage, the melted pre-esterified polymer is polycondensed in the presence of a polycondensation catalyst to form a polyglycolic acid based polymer in the polycondensation reactor. A rare earth catalyst is used as a polycondensation catalyst and added into the polycondensation reactor through a side feeder (2). As a result, polyglycolic acid is formed. In the third stage, the polyglycolic acid is optimized. The optimized product contains polyglycolic acid and glycolide. The proportion of the polyglycolic acid or glycolide can be adjusted by changing the reaction temperature and content of esterification catalyst. The product of polyglycolide acid remains in the reactor while the vapor phase of glycolide is efficiently separated from the polycondensation reactor through a condensation separator (4), which is connected to a vacuum pump (5), and then recovered in a glycolide collection tank (3).

DETAILED DESCRIPTION OF THE INVENTION

The invention provides a three-stage process for producing a product composition containing polyglycolic acid (PGA) and glycolide made from methyl glycolate. The invention is based on the inventors' surprising discovery that the molar ratio of the polyglycolic acid and glycolide in the product composition could be controlled by adjusting the amount of an esterification catalyst and the optimization temperature. The resulting polyglycolic acid has a high monomer conversion rate and high inherent viscosity. This process can be carried out continuously and suitable for industrial amplification.

The main object of the present invention is to use a raw material which is easily obtained by coal chemical industry, methyl glycolate, to prepare a three-kettle process for polyglycolic acid production with the selection of a polycondensation catalyst with high-efficiency to product polyglycolic acid having a high molecular weight, a low yellowness index and excellent chemical and physical properties.

One object of the present invention is to solve the raw material problem associated with polyglycolic acid production. According to this invention, methyl glycolate is used for polyglycolic acid production.

Another object of the present invention is to solve the problem that a high viscosity and high molecular weight product cannot be prepared by using a single catalyst when preparing polyglycolic acid from methyl glycolate. The viscosity of polyglycolic acid prepared by a conventional process can only reach 0.802 dl/g.

A further object of the present invention is to utilize methyl glycolate as a raw material for simultaneous production of polyglycolic acid and glycolide. Adjustment of the process parameters and the polymerization formula may change the yield ratio between the polyglycolic acid and the glycolide.

A process for producing polyglycolic acid from methyl glycolate is provided. The process comprises three stages: esterification (first stage), polycondensation (second stage) and optimization (third stage).

In the first stage, methyl glycolate is esterified in the presence of an esterification catalyst. As a result, a melted pre-esterified polymer is formed.

The methyl glycolate and the esterification catalyst may be added into an esterification reactor. The esterification catalyst may comprise a tin salt, a zinc salt, a titanium salt, a sulfonium salt, a tin oxide, a zinc oxide, a titanium oxide, a sulfonium oxide, or a combination thereof. The molar ratio of the methyl glycolate to the esterification catalyst may be $1:(10^{-5}-10^{-2})$. The esterification reaction may be carried out at a stirring speed of about 1-100 rpm to maintain the surface pressure of the system of about 0-0.5 MPa. The esterification temperature may be about 120-200° C. and the esterification time may be from 30 min to about 4 h.

The esterified product methanol may be gradually removed from the reaction system:

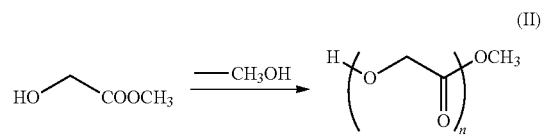

(II)

The methanol content may be about 50-90% of the theoretical value. The resulting pre-esterified polymer may have a viscosity of 0.1-0.3 dl/g.

In the second stage, the melted pre-esterified polymer is polycondensed in the presence of a polycondensation catalyst. As a result, polyglycolic acid based polymer is formed.

The melted pre-esterified polymer may be introduced into a polycondensation reactor. A rare earth catalyst may be used as a polycondensation catalyst.

Rare earth elements can act as stabilizers, catalysts, reinforcing agents, accelerators and coupling agents in polymer materials. Due to the unique valence electron layer structure of rare earth elements, rare earth catalysts have a unique role in catalytic chemistry. The rare earth catalyst has the characteristics of high selectivity and high catalytic activity. Since the polymerization of methyl glycolate is a reversible reaction, the main by-product is a ring-forming reaction, so in order to avoid the reverse reaction, the accelerated removal of methanol is necessary. On the other hand, the rare earth catalyst with higher activity and better selectivity than conventional esterification polycondensation catalysts (tin, zinc, titanium and bismuth) is selected to reduce the activation energy of the reaction and reduce the temperature of the polycondensation reaction. The reduction in temperature tends to reduce the progress of side reactions.

The polycondensation catalyst may comprise an oxide, compound or complex of a rare earth element or a combination thereof. The rare earth element may be selected from the group consisting of cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

The rare earth metal oxide may be in the form of particles. The rare earth metal oxide may have the highest catalytic activity when the particles have a diameter of 2-50 μm, more preferable in the range of 30-45 μm. In one embodiment, the oxide of a rare earth element is $La_2O_3$, preferably in the form of particles. The $La_2O_3$ particles may have a diameter of 35-45 μm, for example, 40 μm. The compound of a rare earth element may be a crystalline rare earth carbonate. The compound of a rare earth element may be a cationic catalyst. In one embodiment, the compound of a rare earth element is crystalline $Ce(HCO_3)_4$.

The coordination complex of a rare earth element may be a rare earth metal complex. For example, the complex of a rare earth element is tris (cyclopentadienyl) lanthanum(III) having formula (I):

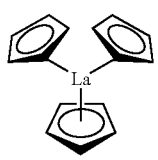

(I)

The molar ratio of the methyl glycolate to the rare earth element in the polycondensation catalyst rare earth metal oxide, compound or complex may be about $1:(10^{-7}\text{-}10^{-4})$, preferably $1:(1\times10^{-5}\text{-}5\times10^{-4})$.

The polycondensation catalyst may further comprise a carrier. The carrier may be an inorganic nanofiller. The inorganic nanofiller may be selected from the group consisting of nano white carbon black, nano calcium carbonate, carbon nanotube, nanofibers and a combination thereof.

The polycondensation reaction may be carried out at a stirring speed of about 1-200 rpm to maintain the absolute pressure of the system to be about $1\text{-}10^3$ Pa. The polycondensation temperature may be about 190-240° C. The methanol content in the polycondensation stage may be about 10-50% of the theoretical value. The reaction time may be about 2-10 hours. The resulting polyglycolic acid-based polymer may have a viscosity of about 0.8-1.2 dl/g. The polyglycolic acid-based polymer contains glycolide and high molecular weight polyglycolic acid.

In the third stage, the polyglycolic acid based polymer is optimized. The term "optimization" used herein refers to a reaction in which the product of polyglycolide acid from polycondensation (second stage) will start reversible reaction and the by-product of glycolide will be obtained simultaneously when the reaction temperature is above 230° C. and the content of esterification catalyst is above 0.1%. The optimization reaction may comprise devolatilization or final polycondensation reaction of the glycolide and the high molecular weight polyglycolic acid in the polyglycolic acid based polymer. The term "devolatilization" used herein refers to separate the low boiling point material including glycolide, monomer and solvent. The term "final polycondensation reaction" used herein refers to improve quality of polyglycolide acid with appropriate viscosity and molecular weight.

The optimization reaction may be carried out in a falling strand devolatilizer, a twin screw devolatilizer, a ribbon stirred reactor, a horizontal disc-ring reactor or a twin-axis self-cleaning reactor.

The optimization may be carried out at a stirring speed of about 1-400 rpm at an optimization temperature of about 200-250° C., under the absolute pressure of about $1\text{-}10^3$ Pa for a reaction time from about 10 min to about 2 h. As a result, a product is produced. The product contains polyglycolic acid and glycolide. For example, the product may contain the glycolide at 1.5-75 wt % and the polyglycolic acid at 25-98.5 wt %, both based on the total weight of the product.

The composition of the product may be adjusted by changing the reaction temperature and the content of the esterification catalyst in the esterification reactor. When the esterification catalyst is added to the methyl glycolate in an amount less than about 0.1 wt % of the total weight of the methyl glycolate, and the optimization reaction temperature is not higher than 230° C., the chemical reaction mainly moves to the polymerization direction, and the product contains mainly polyglycolic acid as extruded from the end of the devolatilizer. For example, the product may contain the polyglycolic acid in an amount greater than about 50, 60, 70, 80, 90, 95 or 99 wt %, based on the total weight of the product.

When the esterification catalyst is added to the methyl glycolate in an amount greater than or equal to about 0.1 wt % of the total weight to the methyl glycolate, and the optimization temperature is higher than 230° C., the side reaction product glycolide is produced mainly by a cyclization reaction and enters the glycolide collection tank through a vacuum devolatilization system. For example, the product may contain the glycolide in an amount greater than about 50, 60, 70, 80 or 90 wt %, based on the total weight of the product.

According to the process of the invention, no separate chambers or reactors are required to produce polyglycolic acid and glycolide separately. Rather, the polyglycolic acid and the glycolide are produced simultaneously in this process and the molar ratio of the polyglycolic acid to the glycolide in the product can be easily modified by adjusting the amount of the esterification catalyst and the reaction temperature.

The catalyst system of the invention can simultaneously achieve a high catalytic efficiency in producing high molecular weight polyglycolic acid and inorganic filling of the polyglycolic acid product to achieve enhanced mechanical strength effect. The polyglycolic acid obtained according to the invention has desirable characteristics such as high molecular weight, high viscosity and low yellowness. The polyglycolic acid may have a weight-average molecular weight of 90,000-200,000, an inherent viscosity of 0.8-1.3 dl/g, a yellowness index (YI) of 9-70, and/or a free acid content of glycolide less than 2 wt %, based on the total weight of the polyglycolic acid.

For each process of the invention, a product is produced. The product may contain glycolide at 1.5-75 wt % and/or the polyglycolic acid at 25-98.5 wt %, both based on the total weight of the product.

A method of changing the amount of the polyglycolic acid in the product produced by the process of the invention is also provided. The method comprises modifying the amount of the esterification catalyst relative to the total weight of the methyl glycolate, adjusting the optimization temperature, or a combination thereof.

The method may further comprise maintaining the esterification catalyst in an amount below 0.1 wt % of the total weight of the methyl glycolate and the optimization temperature not above 230° C. such that the resulting product contains the polyglycolic acid in an amount greater than about 50, 60, 70, 80, 90, 95 or 99 wt %, based on the total weight of the product.

The method may further comprise maintaining the esterification catalyst in an amount not below 0.1 wt % of the total weight of the methyl glycolate and the optimization temperature above 230° C. such that the resulting product contains the glycolide in an amount greater than about 50, 60, 70, 80 or 90 wt %, based on the total weight of the product.

Example 1. Processes 1-32

Processes 1-32 and Comparative 1 were carried out according to the present invention. Their physicochemical parameters are set forth in Table 1. FIG. 1 illustrates the process.

In Process 1, methyl glycolate (MG) and stannous chloride dihydrate (esterification catalyst) (Catalyst A) in an amount of 0 parts by weight of the methyl glycolate reacted in an esterification reactor at stirring Speed A of 30 rpm, 0.1 MPa (gauge pressure) ($PaG_A$/MPa), and 180° C. ($T_A$/° C.) for 90 min ($t_A$/min). The collected methanol content (Methanol Yield A) was 50% of the theoretical value.

The material of the esterification reactor was introduced into the polycondensation reactor, and Ce $(HCO_3)_4$ (polycondensation catalyst) (Catalyst B) in the amount of 5*10-5 parts by weight relative to the weight of the methyl glycolate was added to the polycondensation reactor, reacted at 215° C. ($T_B$/° C. in Table 1) for 240 min ($t_B$/min in Table 1) under an absolute pressure of 100 kPa ($PaA_B$/Pa in Table 1) at 80 rpm (Stirring Speed B in Table 1). The collected methanol content (Methanol Yield B in Table 1) was 48.5% of the theoretical value.

The material in the polycondensation reactor was introduced into the optimization reactor at 180 rpm (stirring Speed C in Table 1). The reaction was carried out under the conditions of 225° C. ($T_C$/° C. in Table 1) under an absolute pressure of 50 Pa ($PaA_C$/Pa in Table 1) for 45 min ($t_C$/min in Table 1). The finally collected glycolide content (GL Yield/% in Table 1) was 2% and the polyglycolic acid content was 98%.

Processes 2-32 were carried out in the same way as that for Process 1 except the parameters set forth in Table 1.

Processes 33 and 34 were carried out in the same way as that for Process 3 except the parameters set forth in Table 2.

Comparative Process 1 was carried out. Methyl glycolate and stannous chloride dihydrate (esterification catalyst) at $2.5*10^{-3}$ parts by weight relative to the weight of the methyl glycolate were heated to 150° C., held for 60 min, heated to 180° C., slowly vacuumed to absolute pressure of 4,000 Pa, after the amount of the methanol formed reached 85%, the solid phase polycondensation was carried out at a polycondensation temperature of 180° C. under the absolute pressure of 70 Pa for 6,000 min.

The products produced from Processes 1-32 and Comparative Process 1 were evaluated in the following tests and the results are shown in Table 1.

A. Weight-Average Molecular Weight and its Distribution

A sample is dissolved in a solution of five mmol/L sodium trifluoroacetate in hexafluoroisopropanol to prepare a solution of 0.05-0.3 wt % (mass fraction). The solution is then filtered with a 0.4 μm pore size polytetrafluoroethylene filter. 20 μL of the filtered solution is added to the Gel permeation chromatography (GPC) injector for determination of molecular weight of the sample. Five standard molecular weights of methyl methacrylate with different molecular weights are used for molecular weight correction.

B. Yellowness Index YI Test

A Copolymer Having a Smooth Surface and No Obvious Convexity was Selected. The yellowness index (YI) of the product was determined by using NS series color measuring instrument of 3 nh company. According to ASTM E313, the measurement was carried out three times under the conditions of 10 degree observation angle, D65 observation light source and reflected light measurement, and the average value was calculated to determine the yellowness index (YI) of the copolymer.

C. Melt Index (MI) Test

The melt index (MFR) of a copolymer is tested according to the following m: 1) drying the copolymer in a vacuum drying oven at 105° C.; 2) setting the test temperature of the test instrument to 230° C. and preheating the instrument; 3) loading 4 g of the dried copolymer into a barrel through a funnel and inserting a plunger into the barrel to compact the dried copolymer into a rod; 4) keeping the dried copolymer in the rod for 1 min with a weight of 2.16 kg pressing on top of the rod, and then cutting a segment every 30 s to obtain a total of five segments; 5) weighing the mass of each sample and calculating its MFR. MFR=600 W/t (g/10 min), where W is the average mass per segment of the sample and t is the cutting time gap for each segment.

D. Inherent Viscosity

1) Take a mass of m1 polyglycolic acid sample and hexafluoroisopropanol solvent in an amount of m2 to prepare a solution with a concentration of 0.125 g/dL, of which m1/m2=0.125/40;

2) Fully automatic with TN-7 Determination by inherent viscosity meter, the measurement condition is (25±0.1) ° C. constant temperature oil bath, calculation formula (III)

$$[\eta]=[2(\eta_{sp}-\ln \eta_r)]^{1/2}/c \qquad (III)$$

E. Determination of Free Acid 0.5 g of a sample was weighed into an Erlenmeyer flask, about 20 ml of dimethyl sulfoxide was added, and the glycolide sample solution was subjected to potentiometric titration with a solution of 0.01 mol/L of potassium hydroxide.

Although the invention is illustrated and described herein with reference to specific embodiments, the invention is not intended to be limited to the details shown. Rather, various modifications may be made in the details within the scope and range of equivalents of the claims without departing from the invention.

TABLE 1

| No. | MG | Catalyst A | stirring Speed A/ RPM | PaG$_A$/ MPa | T$_A$/ °C | t$_A$/ min | Methanol Yield A/ % | η$_A$/ (dl/g) | Catalyst B | stirring Speed B/ RPM | PaA$_B$/ Pa | T$_B$/ °C | t$_B$/ min | Methanol Yield B/ % | η$_B$/ (dl/g) | stirring Speed C/ RPM | PaA$_C$/ Pa | T$_C$/ °C | t$_C$/ min | Glycolide Yield/ % | η$_C$/ (dl/g) | Mw | MI/ (g/10 min) | YI |
|---|---|---|---|---|---|---|---|---|---|---|---|---|---|---|---|---|---|---|---|---|---|---|---|---|
| 1 | 1 | 0 | 30 | 0.1 | 180 | 90 | 50 | 0.12 | 5*10$^{-5}$ | 80 | 100 | 215 | 240 | 48.5 | 0.8 | 180 | 50 | 225 | 45 | 2.0 | 0.85 | 93000 | 47 | 13 |
| 2 | 1 | 0.01 | 30 | 0.1 | 180 | 90 | 90 | 0.3 | 5*10$^{-5}$ | 80 | 100 | 215 | 240 | 9.5 | 1.11 | 180 | 50 | 225 | 45 | 1.7 | 1.2 | 152800 | 25 | 65 |
| 3 | 1 | 10$^{-4}$ | 30 | 0.1 | 180 | 90 | 85 | 0.28 | 5*10$^{-5}$ | 80 | 100 | 215 | 240 | 14.6 | 1.1 | 180 | 50 | 225 | 45 | 1.5 | 1.3 | 169800 | 10 | 9 |
| 4 | 1 | 10$^{-4}$ | 1 | 0.1 | 180 | 90 | 59 | 0.18 | 5*10$^{-5}$ | 80 | 100 | 215 | 240 | 40.2 | 1.03 | 180 | 50 | 225 | 45 | 1.6 | 1.08 | 120000 | 35 | 36 |
| 5 | 1 | 10$^{-4}$ | 100 | 0.1 | 180 | 90 | 80 | 0.27 | 5*10$^{-5}$ | 80 | 100 | 215 | 240 | 19 | 1.2 | 180 | 50 | 225 | 45 | 1.23 | 1.22 | 156700 | 22 | 24 |
| 6 | 1 | 10$^{-4}$ | 30 | 0 | 180 | 90 | 83 | 0.27 | 5*10$^{-5}$ | 80 | 100 | 215 | 240 | 16.1 | 1.2 | 180 | 50 | 225 | 45 | 1.55 | 1.22 | 157900 | 22 | 20 |
| 7 | 1 | 10$^{-4}$ | 30 | 0.5 | 180 | 90 | 69 | 0.2 | 5*10$^{-5}$ | 80 | 100 | 215 | 240 | 30.2 | 1.14 | 180 | 50 | 225 | 45 | 2.35 | 1.18 | 148600 | 26 | 29 |
| 8 | 1 | 10$^{-4}$ | 30 | 0.1 | 120 | 90 | 85 | 0.28 | 5*10$^{-5}$ | 80 | 100 | 215 | 240 | 14.6 | 1.2 | 180 | 50 | 225 | 45 | 2.5 | 1.3 | 163000 | 19 | 17 |
| 9 | 1 | 10$^{-4}$ | 30 | 0.1 | 200 | 90 | 85 | 0.28 | 5*10$^{-5}$ | 80 | 100 | 215 | 240 | 14.6 | 1.2 | 180 | 50 | 225 | 45 | 1.98 | 1.3 | 161500 | 20 | 20 |
| 10 | 1 | 10$^{-4}$ | 30 | 0.1 | 180 | 30 | 85 | 0.28 | 5*10$^{-5}$ | 80 | 100 | 215 | 240 | 14.6 | 1.2 | 180 | 50 | 225 | 45 | 1.77 | 1.3 | 164300 | 19 | 18 |
| 11 | 1 | 10$^{-4}$ | 30 | 0.1 | 180 | 240 | 85 | 0.28 | 5*10$^{-5}$ | 80 | 100 | 215 | 240 | 14.6 | 1.2 | 180 | 50 | 225 | 45 | 1.58 | 1.3 | 162700 | 19 | 18 |
| 12 | 1 | 10$^{-4}$ | 30 | 0.1 | 180 | 90 | 85 | 0.28 | 10$^{-6}$ | 80 | 100 | 215 | 240 | 14.6 | 1.2 | 180 | 50 | 225 | 45 | 1.93 | 1.3 | 165000 | 17 | 16 |
| 13 | 1 | 10$^{-4}$ | 30 | 0.1 | 180 | 90 | 85 | 0.28 | 10$^{-3}$ | 80 | 100 | 215 | 240 | 14.6 | 1.2 | 180 | 50 | 225 | 45 | 1.64 | 1.3 | 166600 | 15 | 12 |
| 14 | 1 | 10$^{-4}$ | 30 | 0.1 | 180 | 90 | 85 | 0.28 | 5*10$^{-5}$ | 1 | 100 | 215 | 240 | 14 | 0.96 | 180 | 50 | 225 | 45 | 1.77 | 1.12 | 139800 | 31 | 31 |
| 15 | 1 | 10$^{-4}$ | 30 | 0.1 | 180 | 90 | 85 | 0.28 | 5*10$^{-5}$ | 200 | 100 | 215 | 240 | 14.4 | 0.93 | 180 | 50 | 225 | 45 | 2.01 | 1.1 | 135600 | 33 | 33 |
| 16 | 1 | 10$^{-4}$ | 30 | 0.1 | 180 | 90 | 85 | 0.28 | 5*10$^{-5}$ | 80 | 1 | 215 | 240 | 14.7 | 1.07 | 180 | 50 | 225 | 45 | 1.58 | 1.18 | 145900 | 28 | 27 |
| 17 | 1 | 10$^{-4}$ | 30 | 0.1 | 180 | 90 | 85 | 0.28 | 5*10$^{-5}$ | 80 | 1000 | 215 | 240 | 14 | 0.86 | 180 | 50 | 225 | 45 | 2.18 | 1.05 | 112000 | 39 | 23 |
| 18 | 1 | 10$^{-4}$ | 30 | 0.1 | 180 | 90 | 85 | 0.28 | 5*10$^{-5}$ | 80 | 100 | 190 | 240 | 13.7 | 0.88 | 180 | 50 | 225 | 45 | 1.78 | 1.06 | 112500 | 38 | 35 |
| 19 | 1 | 10$^{-4}$ | 30 | 0.1 | 180 | 90 | 85 | 0.28 | 5*10$^{-5}$ | 80 | 100 | 240 | 240 | 14.2 | 1.07 | 180 | 50 | 225 | 45 | 1.59 | 1.1 | 132700 | 36 | 44 |
| 20 | 1 | 10$^{-4}$ | 30 | 0.1 | 180 | 90 | 85 | 0.28 | 5*10$^{-5}$ | 80 | 100 | 215 | 120 | 14.1 | 1.13 | 180 | 50 | 225 | 45 | 2.13 | 1.2 | 151600 | 25 | 29 |
| 21 | 1 | 10$^{-4}$ | 30 | 0.1 | 180 | 90 | 85 | 0.28 | 5*10$^{-5}$ | 80 | 100 | 215 | 600 | 14.5 | 1.15 | 180 | 50 | 225 | 45 | 2.47 | 1.2 | 150000 | 25 | 35 |
| 22 | 1 | 10$^{-4}$ | 30 | 0.1 | 180 | 90 | 85 | 0.28 | 5*10$^{-5}$ | 80 | 100 | 215 | 240 | 14.6 | 1.2 | 1 | 50 | 225 | 45 | 2.02 | 1.21 | 154400 | 24 | 25 |
| 23 | 1 | 10$^{-4}$ | 30 | 0.1 | 180 | 90 | 85 | 0.28 | 5*10$^{-5}$ | 80 | 100 | 215 | 240 | 14.6 | 1.2 | 400 | 50 | 225 | 45 | 1.93 | 1.25 | 160000 | 20 | 18 |
| 24 | 1 | 10$^{-4}$ | 30 | 0.1 | 180 | 90 | 85 | 0.28 | 5*10$^{-5}$ | 80 | 100 | 215 | 240 | 14.6 | 1.2 | 180 | 1*10$^3$ | 225 | 45 | 1.88 | 1.31 | 170000 | 9 | 10 |
| 25 | 1 | 10$^{-4}$ | 30 | 0.1 | 180 | 90 | 85 | 0.28 | 5*10$^{-5}$ | 80 | 100 | 215 | 240 | 14.6 | 1.2 | 180 | 50 | 200 | 45 | 1.75 | 1.21 | 154000 | 24 | 22 |
| 26 | 1 | 10$^{-4}$ | 30 | 0.1 | 180 | 90 | 85 | 0.28 | 5*10$^{-5}$ | 80 | 100 | 215 | 240 | 14.6 | 1.2 | 180 | 50 | 250 | 45 | 2.06 | 1.23 | 159100 | 20 | 21 |
| 27 | 1 | 10$^{-4}$ | 30 | 0.1 | 180 | 90 | 85 | 0.28 | 5*10$^{-5}$ | 80 | 100 | 215 | 240 | 14.6 | 1.2 | 180 | 50 | 225 | 10 | 2.11 | 1.17 | 146700 | 27 | 48 |
| 28 | 1 | 10$^{-4}$ | 30 | 0.1 | 180 | 90 | 85 | 0.28 | 5*10$^{-5}$ | 80 | 100 | 215 | 240 | 14.6 | 1.2 | 180 | 50 | 225 | 120 | 2.47 | 1.22 | 158300 | 22 | 25 |
| 29 | 1 | 10$^{-4}$ | 30 | 0.1 | 180 | 90 | 85 | 0.28 | 5*10$^{-5}$ | 80 | 100 | 215 | 240 | 14.6 | 1.2 | 180 | 50 | 225 | 45 | 2.22 | 1.21 | 153200 | 25 | 35 |
| 30 | 1 | 10$^{-4}$ | 30 | 0.1 | 180 | 90 | 85 | 0.28 | 5*10$^{-5}$ | 80 | 100 | 215 | 240 | 14.6 | 1.2 | 180 | 50 | 245 | 45 | 33 | 1.0 | 100400 | 41 | 40 |
| 31 | 1 | 10$^{-3}$ | 30 | 0.1 | 180 | 90 | 87 | 0.3 | 5*10$^{-5}$ | 80 | 100 | 215 | 240 | 12.6 | 1.2 | 180 | 50 | 245 | 45 | 25 | 0.8 | 90000 | 50 | 69 |
| 32 | 1 | 10$^{-3}$ | 30 | 0.1 | 180 | 90 | 87 | 0.3 | 5*10$^{-5}$ | 80 | 100 | 215 | 240 | 12.6 | 1.2 | 180 | 50 | 225 | 45 | 75 | 0.96 | 95300 | 45 | 55 |
| C2 | 1 | 10$^{-4}$ | 30 | 0.1 | 180 | 90 | 85 | 0.28 | 0 | 80 | 100 | 215 | 240 | 11 | 0.8 | 180 | 70 | 225 | 45 | 16 | 0.9 | 100000 | 38 | 39 |
| C1 | 1 | 2.5*10$^{-3}$ | 30 | 0.1 | 150 | 60 | — | 0.352 | 0 | 80 | 4000 | 180 | — | — | — | — | — | 180 | 6000 | 5 | 0.802 | — | — | — |

NOTE:
MG is methyl glycolate. Catalyst A is esterification catalyst stannous chloride dihydrate. Catalyst B is polycondensation catalyst Ce(HCO$_3$)$_4$ or La$_2$O$_3$ or tris (cyclopentadienyl) lanthanum (III). PaG is gauge pressure. PaA is absolute pressure. T is reaction temperature. t is reaction time. η is inherent viscosity. GL is glycolide. Mw is weight-average molecular weight. YI is yellowness index. MI is the melt index.

TABLE 2

Carrier effects

| No. | Catalyst B | Carrier | Methanol Yield B/% | $\eta_B$/(dl/g) | $\eta_C$/(dl/g) | Mw | MI/(g/10 min) | Tensile Stress/MPa |
|---|---|---|---|---|---|---|---|---|
| 3 | Ce(HCO$_3$)$_4$ | — | 14.6 | 1.2 | 1.3 | 169800 | 10 | 110 |
| 33 | Ce(HCO$_3$)$_4$ | Nano calcium carbonate | 14.8 | 1.22 | 1.33 | 174000 | 8 | 125 |
| 34 | Ce(HCO$_3$)$_4$ | Carbon nanotube | 14.9 | 1.24 | 1.35 | 178500 | 8 | 132 |

What is claimed:

1. A process for producing polyglycolic acid and glycolide from methyl glycolate, comprising:
   (a) esterifying methyl glycolate in the presence of an esterification catalyst, whereby a melted pre-esterified polymer is formed;
   (b) polycondensing the melted pre-esterified polymer in the presence of a polycondensation catalyst, whereby polyglycolic acid based polymer is formed; and
   (c) an optimized reaction section optimizes the reaction of the polyglycolic acid-based polymer at an optimized temperature of 200-250° C., so as to controllably produce a polyglycolic acid and/or glycolide.

2. The process of claim 1, wherein the esterification catalyst comprises one or more of tin salts, zinc salts, titanium salts, and bismuth salts or oxides.

3. The process of claim 2, wherein the methyl glycolate and the esterification catalyst have a molar ratio of 1:($10^{-5}$-$10^{-2}$).

4. The process of claim 1, wherein the polycondensation catalyst comprises an oxide, compound or complex of a rare earth element selected from the group consisting of cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y), or a combination thereof.

5. The process of claim 4, wherein the oxide of a rare earth elements is the particle with the diameter of 2-50 μm.

6. The process of claim 4, wherein the compound of a rare earth element is the crystalline carbonate cationic catalyst.

7. The process of claim 4, wherein the complex of a rare earth element is tris (cyclopentadienyl) lanthanum(III) having formula (I):

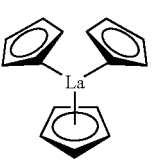

(I)

8. The process of claim 4, wherein the methyl glycolate and the rare earth element have a molar ratio of 1:($10^{-7}$-$10^{-4}$).

9. The process of claim 4, wherein the polycondensation catalyst further comprises an inorganic nanofiller selected from the group consisting of nano white carbon black, nano calcium carbonate, carbon nanotube, nanofibers and a combination thereof.

10. The process of claim 1, wherein the optimization reaction comprises devolatilization or final polycondensation reaction of the polyglycolic acid based polymer in a falling strand devolatilizer, a twin screw devolatilizer, a ribbon stirred reactor, a horizontal disc-ring reactor or a twin-axis self-cleaning reactor.

11. The process of claim 1, wherein the product contains the glycolide at 1.5-75 wt % and the polyglycolic acid at 25-98.5 wt %, both based on the total weight of the product.

12. The process of claim 1, wherein the esterification catalyst is present in an amount less than 0.1 wt % of the total weight of the methyl glycolate, and the optimization temperature is not above 230° C., the product contains the polyglycolic acid in an amount greater than 95 wt %, based on the total weight of the product.

13. The process of claim 1, wherein the esterification catalyst is present in an amount no less than 0.1 wt % of the total weight of the methyl glycolate, and the optimization temperature is above 230° C., the product contains the glycolate in an amount greater than 70 wt %, based on the total weight of the products.

14. The process of claim 1, wherein the polyglycolic acid has a weight-average molecular weight of 90,000-200,000.

15. The process of claim 1, wherein the polyglycolic acid has an inherent viscosity of 0.8-1.3 dl/g.

16. The process of claim 1, wherein the polyglycolic acid has a yellowness index (YI) of 9-70.

17. The process of claim 1, wherein the polyglycolic acid has a free acid content of glycolide less than 2 wt %, based on the total weight of the polyglycolic acid.

18. A product produced by the process of claim 1, wherein the product contains the glycolide at 1.5-75 wt % and the polyglycolic acid at 25-98.5 wt %, both based on the total weight of the product.

19. A method of changing the amount of the polyglycolic acid in the product produced by the process of claim 1, comprising modifying the amount of the esterification catalyst relative to the total weight of the methyl glycolate, adjusting the optimization temperature, or a combination thereof.

20. The method of claim 19, further comprising maintaining the esterification catalyst in an amount below 0.1 wt % of the total weight of the methyl glycolate and the optimization temperature not above 230° C., whereby the product contains the polyglycolic acid in an amount greater than 95 wt %, based on the total weight of the product.

21. The method of claim 19, further comprising maintaining the esterification catalyst in an amount not below 0.1 wt % of the total weight of the methyl glycolate and the optimization temperature above 230° C., whereby the product contains the glycolide in an amount greater than 70 wt %, based on the total weight of the product.

* * * * *